United States Patent

Cohn

Patent Number: 5,897,506
Date of Patent: Apr. 27, 1999

[54] PULSE RATE MONITOR FOR ALLERGY DETECTION AND CONTROL

[76] Inventor: Lipe Cohn, 16 Hayes Ct., Monroe, N.Y. 10950

[21] Appl. No.: 08/933,957

[22] Filed: Sep. 19, 1997

[51] Int. Cl.$^6$ ........................................................ A61B 5/00
[52] U.S. Cl. ............................................ 600/556; 600/503
[58] Field of Search ................................... 600/500, 502, 600/503, 556

[56] References Cited

U.S. PATENT DOCUMENTS

| | | | |
|---|---|---|---|
| 4,224,948 | 9/1980 | Cramer et al. | 600/503 |
| 4,367,752 | 1/1983 | Jimenez et al. | 600/502 |
| 4,566,461 | 1/1986 | Lubell et al. | 600/502 |
| 4,802,488 | 2/1989 | Eckerle | 600/503 |
| 4,807,639 | 2/1989 | Shimizu et al. | 600/503 |
| 4,819,657 | 4/1989 | Kraft et al. | 600/556 |
| 5,197,489 | 3/1993 | Conlan | 600/503 |
| 5,267,568 | 12/1993 | Takara | 600/500 |

FOREIGN PATENT DOCUMENTS

| | | | |
|---|---|---|---|
| 002603-473 | 3/1988 | France | 600/503 |

*Primary Examiner*—Max Hindenburg
*Assistant Examiner*—Charles Marmor, II
*Attorney, Agent, or Firm*—Graham & James LLP

[57] ABSTRACT

A wrist wearable device for the detection and monitoring of possible allergy symptoms and relation to specific triggering conditions. The device has a visual display and is operatively attached to a human pulse point. It also has a clock/calendar timer, pulse measurement mechanism and alarm, an addressable memory with an input control, preinstalled icons and user controlled identification symbols and a logic circuit system. The device is adapted to be worn constantly with pulse measurements, related to time and date, being stored in memory. Average pulse rates are determined, based on time and day of week and stored in memory. Excessively elevated pulse rate spikes (relative to determined average pulse rates) are monitored and the wearer is warned of the elevated level. Absent ostensible physical and emotional causes, elevated pulse rates are attributable to allergic reactions. To ascertain the source of the allergy, the wearer of the device, scrolls through pre-programmed icon representations of common allergy inducing foods or conditions and sets the device to monitor conditions present at the time of pulse rate spike. Thereafter, the device is addressed by the wearer when any or all of the conditions are replicated. The device relates time (time and day) with elevated pulse rate and replicated condition and stores pulse spikes in memory. After a pre-determined time period, correlated and stored conditions are downloaded for analysis of possible allergic reactions and causes.

4 Claims, 1 Drawing Sheet

PULSE RATE MONITOR FOR ALLERGY DETECTION AND CONTROL

FIELD OF THE INVENTION

This invention relates to procedures and devices used in the determination and monitoring of possible allergic reactions and specifically relates to long term monitoring of possible allergic trigger conditions.

BACKGROUND OF THE INVENTION

Various procedures exist for determining the cause of a patient's allergic reactions or even that an allergic reaction exists. Such tests usually involve the use of a series of minor dermal inoculations with small doses of common sources of allergies and an inspection to see if there is a local skin reaction. Oftentimes determination of the source for an allergy is much less straightforward and a source of allergy is not as forthcoming. Under such circumstance the patient is advised to keep logs of lifestyles and conditions during occurrences of untoward reactions in order to try to relate the reaction to foods or drinks being ingested, inhalants, tactile irritants, ambient conditions and the like, which are or may be present during adverse reactions. This procedure is utilized in an effort to narrow down, over time, the scope of suspected sources. This is however, an onerous task which is often not scrupulously (or even properly) followed by patients. It is also particularly difficult with respect to children who are unable to follow directions properly and usually requires adult supervision (which may not even be at hand) to ascertain conditions and to help with recordal.

In addition, some discomfort conditions might not even be allergic reactions yet they may be noted as such. Even allergic reactions are not consistent in occurrence and may in fact require a confluence of factors before a trigger point is reached. Thus, a cat's presence may or may not trigger an allergic reaction depending on other atmospheric conditions and ventilation. Record keeping, according to the prior art, is onerous and often difficult to reconcile and evaluate.

SUMMARY OF THE INVENTION

It is accordingly an object of the present invention to provide a device with pulse rate detection means and alarm means, triggered by pulse rates above an average norm, as determined by the device, with the device also having event memory means, whereby the patient, being warned of an allergy reaction incident, can simply enter into the device a preprogrammed nature of conditions proximate to the allergy reaction event.

It is a further object of the present invention to provide such device in a wrist wearable form whereby it can also function as a wrist watch in proximity to a pulse point for pulse monitoring.

It is yet another object of the present invention to provide the device with scrollable icons, indicative of allergy inducing foods and conditions which can simply be pointed to by an input device for entry thereof, as being present at an allergy alarm signal.

These and other objects, features and advantages of the present application will become more evident from the following discussion and drawings in which:

SHORT DESCRIPTION OF THE DRAWINGS

FIG. 1 schematically depicts the device of the present invention with pulse engagement means for the detection of pulse rates;

DETAILED DESCRIPTION OF THE INVENTION

Figure 1:
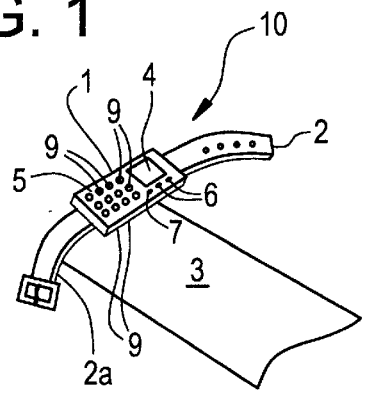

It has been discovered that allergic reactions are almost always accompanied by an abnormal and substantial quickened pulse rate. Accordingly, a monitoring of pulse rates and a detection of increased pulse rate, not otherwise attributable to physical causes, e.g., exercise; or emotional stress, is reasonably attributable to an allergic reaction of some sort and is a fairly reliable indicator of an allergy condition.

In accordance with the present invention, a device is used to constantly monitor pulse rates (over a pre-determined period of time, e.g., several weeks) and to establish average norms related to times of day (e.g., sleep, travel, repeated activities, etc.), as well as to monitor and record incidents of elevated pulse levels, as a function of time (time and day). The device is provided with addressable memory means to automatically record the incidence of allergy reactions and to record, by icon driven entry by the patient (simplified entry sufficient for even a child to enter), possible sources of the allergy reaction.

In configuration, the device of the present invention preferably comprises a wrist wearable device for the detection and monitoring of possible allergy symptoms and relation to specific triggering conditions. The device has a visual display and is operatively attached to a human pulse point. It also has a clock/calendar timer, pulse measurement mechanism and alarm, an addressable memory with an input control, preinstalled icons and user controlled identification symbols and a logic circuit system. The device is adapted to be worn constantly, with pulse measurements, related to time and date, being stored in memory.

Average pulse rates are determined, based on time and day of week and stored in memory. Excessively elevated pulse rate spikes (relative to determined average pulse rates) are monitored and the wearer is warned of the elevated level. Absent ostensible physical and emotional causes, elevated pulse rates are attributable to allergic reactions. To ascertain the source of the allergy, the wearer of the device, scrolls through pre-programmed icon representations of common allergy inducing foods or conditions and sets the device to monitor conditions present at the time of pulse rate spike. Thereafter, the device is addressed by the wearer when any or all of the conditions are replicated. The device relates time (time and day) with elevated pulse rate and replicated condition and stores pulse spikes in memory. After a predetermined time period, correlated and stored conditions are downloaded for analysis of possible allergic reactions and causes.

Since various activities during the day result in different pulse rates (lower during night time and sleeping and higher during day time with work, walking and exercise activities), the device of the present invention correlates an average pulse rate to a particular time period during the day in making a determination of excessively elevated pulse rates from a base average established for a particular time period. In addition pulse rate elevation is generally about a 20% increase for a sustained period of several minutes. Thus, in an example of a possible allergy condition, someone trying to determine if cats cause a reaction is able to immediately determine if proximity to a cat causes an alarm setting to go off, thereby indicating an elevated pulse level or the absence of one. There is both immediate feedback and a recordal of incidents. With each warning the patient is able to scroll through a series of icons until a representation of an animal or cat is visible in the view screen of the device. The cat icon is selected and the device correlates and stores the incident as being a reaction triggered by the presence of a cat or whatever else is appropriate. A series of events with common denominators establishes the nature of the allergy. This series of events (i.e. correlations of increased pulse level with iconically entered conditions) is downloadable from the device for analysis thereof, as required.

Various icons include representations of foods which are common to allergies such as strawberries, peanut butter, milk, etc., or animals such as cats, dogs, horses, as well as environmental conditions of pollen, smog, smoke, trees, flowers, etc. In unusual cases it is preferred that the device includes the ability to enter user specified conditions for which there is no pre-set icon. Under such conditions, the patient enters the condition with a selected alpha, alphanumeric, or numeric representation and each subsequent entry cumulates conditions for the same representation. Thus, an alpha entry for "jbs" as representing jelly beans will cumulate information for each entry of "jbs" to establish whether or not there is an allergic reaction to jelly beans over cumulated periods of time and proximity.

DETAILED DESCRIPTION OF THE DRAWINGS AND THE PREFERRED EMBODIMENT

With respect to the drawings, in FIG. 1 the device 10 of the present invention is shown in the form of a wristwatch with a small body part 1 and a wristband 2. The wristband has a pulse sensor 2a in the wrist contacting portion thereof, to continuously take the pulse of the wearer 3 and to transmit it to computer and memory portions of body part 1 for analysis and storage. The body part 1 has a face 4 in which there is a normal display of time, day and date and in which displays for operation of the device are displayed. Alphanumeric button keyboard 5 allows for input access and instructions. Scroll keys 6 and selection key 7 permit scrolling of stored icons of possible allergy source conditions, e.g., strawberry 8, shown in the display 4, and the selection thereof respectively. Buttons 9 perform standard watch control functions (time and date set, wake-up alarm, etc.). The device, as shown, provides the dual functions of watch and monitoring device whereby the device is unobtrusive, without interfering with normal activities, and is constantly worn as a normal watch without the need for a separate wearable item.

Figure 2:
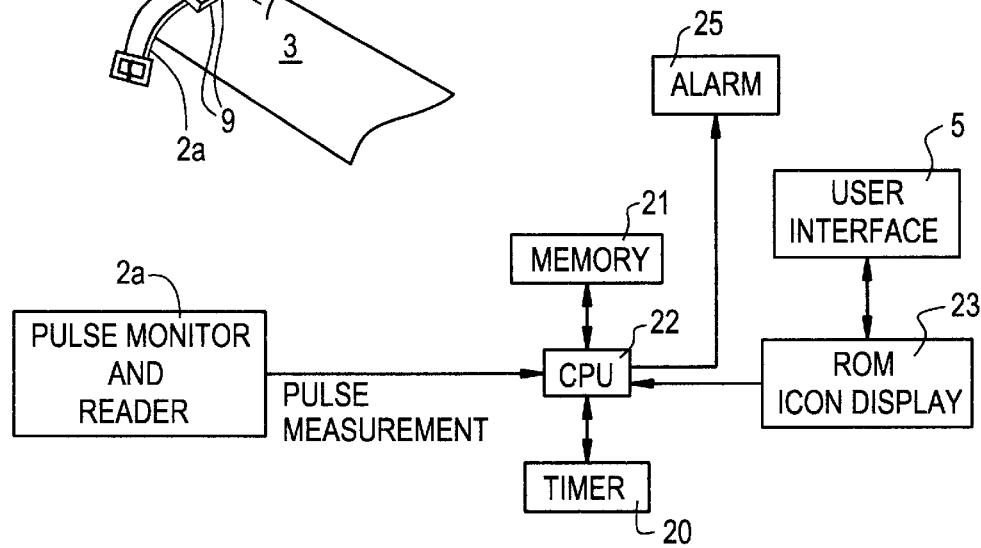
FIG. 2 is a block diagram schematically depicting the elements of the device.
Figure 2A:
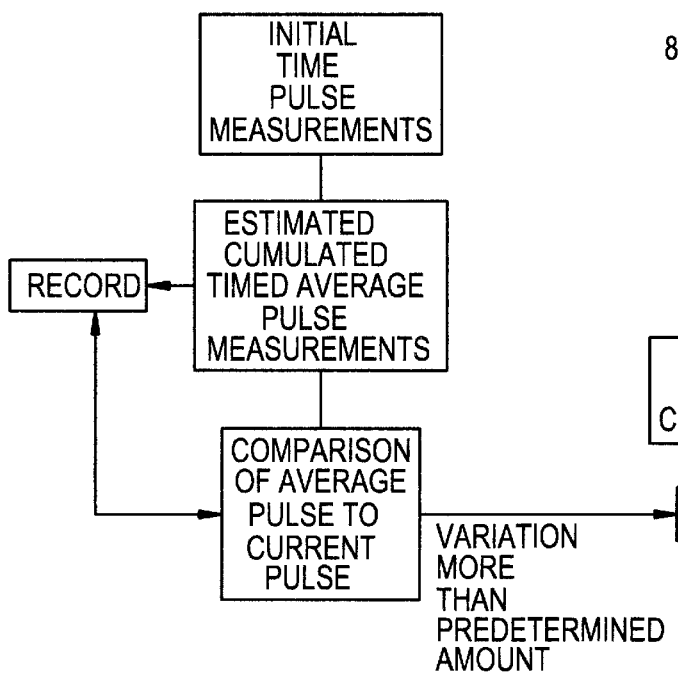
FIG. 2a is a flow chart indicating the manner in which the device is utilized for record keeping and evaluation.
Figure 2A:
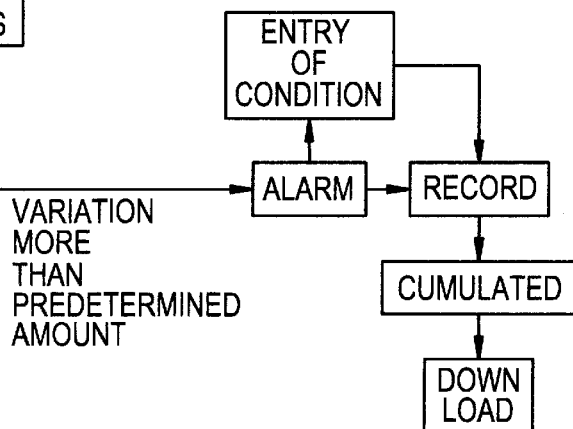
Figure 3:
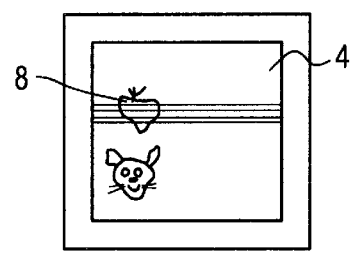
FIG. 3 is a typical viewing screen of the device with allergy indicating icons.

As schematically shown in FIG. 2, the integrated circuit elements within the body part 1 include the timer elements (shared with the watch function) 20 of time and day of the week. As set forth in flow chart of FIG. 2a, all pulse rate data received from the pulse sensor 2a is initially tagged with a time and day and then stored in memory 21. Over an initial period of several days or a week, the cpu 22 of the device establishes an average pulse rate for specific replicated time and day blocks and stores it in memory 21. Thereafter, with the average pulse rates established and time correlated, the device is set on monitoring function to monitor anomalous pulse rates relative to time tagged average pulse rates. If an anomalous pulse rate reaches a predetermined critical level, the event is time recorded in memory and an alarm 25 is triggered to advise the wearer to enter environmental condition data for recordation with the anomalous pulse rate. The user, uses button keys 6 to scroll through a set of icon representations of allergy factors and conditions (for example the set icon in FIG. 3 of a strawberry 8) and selects those present at the time of the alarm by means of selection button key 7. Nothing else is required of the patient. If there is no relevant icon, but the patient is aware of an unusual condition, the patient adds an alphanumeric symbol to designate such condition (the patient should however be consistent in subsequent entries for the same condition). The cpu links the condition to the time-stamped event and stores it in memory.

After a predetermined period of time, memory is accessed and downloaded with a listing of event occurrences (with normal and anomalous pulse rates), times (including day and date) and the entered icons (or word description thereof) or alphanumerics. Reoccurrence of certain icons or alphanumerics is a strong indicator of the source of any allergy condition which can then be more positively tested by established medical procedures.

Wrist deployable pulse monitor devices are currently readily available (generally used for monitoring a person's pulse rate with respect to treatment or diagnosis of cardiac conditions). A simple cpu device (to assimilate and establish timed average pulse rates, to compare established average pulse rates to new pulse rate reading, and to record and link timed anomalous pulse rates with entered conditions) is integrated with the input thereof. The cpu 22 itself is integrated with a watch timer chip 20, with preprogrammed read-only memory (ROM) 23, addressable memory 21 and a miniature keyboard 5 akin to those found on calculator watches but with alphanumerics. Allergy icons are preprogrammed into ROM for scrolled display and are usually understandable pictorial representations of common allergy sources, such as exemplified in FIG. 3.

It is understood that the above discussion, drawings and preferred embodiment are merely exemplary of the present invention and that changes in structure, features and components, as well as operation, may be made without departing from the scope of the present invention as defined in the following claims.

What is claimed is:

1. A wearable device for the detection and monitoring of possible allergy symptoms and relation to specific triggering conditions, comprising:
   a) means for operatively attaching the device to a pulse point of a wearer thereof with means for continually measuring pulse rate of a wearer of the device with individual pulse rate measurements;
   b) cpu means with integrated timer means for receiving the individual pulse rate measurements and for time encoding the individual pulse rate measurements; said cpu means further comprising means for establishing time based average pulse rates from the individual pulse rate measurements;
   c) memory means for storage of the time encoded individual pulse rate measurements;
   d) means for comparing the time based average pulse rates to actual pulse rate measurements at the time;
   e) alarm means triggered by the means for comparing the time based average pulse rates to actual pulse rate measurements, for alerting the wearer of a predetermined difference in pulse rate therebetween;
   f) memory means for entry of the time based difference in pulse rate and addressable memory means for wearer entry of allergy triggering conditions, external to the wearer, at the time of triggering of the alarm, with means for linking and recording in said memory means for entry of the time based difference in pulse rate and the wearer entered allergy triggering conditions; and g) means for downloading a cumulative list of linked time based alarms and entered allergy triggering conditions.

2. The device of claim 1, wherein the device comprises a visual display and a pre-programmed scrollable icon display of a plurality of selectable allergy conditions for use by the wearer for the entry of allergy triggering conditions.

3. The device of claim 2, wherein the device further comprises means for alphanumeric indicia as additional means for the wearer entry of allergy triggering conditions.

4. The device of claim 3, wherein the device is adapted to be worn on a wrist of the wearer and wherein the timer means further provides measurement and display of current time.

* * * * *